United States Patent [19]
McEwan

[11] Patent Number: 5,966,090
[45] Date of Patent: Oct. 12, 1999

[54] DIFFERENTIAL PULSE RADAR MOTION SENSOR

[76] Inventor: Thomas E. McEwan, 1734 Cairo St., Livermore, Calif. 94550

[21] Appl. No.: 09/039,680

[22] Filed: Mar. 16, 1998

[51] Int. Cl.⁶ .................................................. G01S 13/56
[52] U.S. Cl. .............................. 342/27; 342/28; 340/541; 340/552
[58] Field of Search ........................ 342/27, 28; 340/541, 340/552, 553, 554, 561, 565, 567

[56] References Cited

U.S. PATENT DOCUMENTS

| | | | |
|---|---|---|---|
| 3,175,214 | 3/1965 | Ramsay et al. | 343/13 |
| 3,195,130 | 7/1965 | Adrian | 343/12 |
| 3,423,754 | 1/1969 | Gunn | 343/17.1 |
| 3,631,351 | 12/1971 | Paine et al. | 328/133 |
| 3,680,100 | 7/1972 | Woerrlein | 343/11 R |
| 3,721,980 | 3/1973 | Oister | 343/9 |
| 3,806,795 | 4/1974 | Morey | 324/6 |
| 3,898,655 | 8/1975 | Tresselt | 343/7.5 |
| 3,932,871 | 1/1976 | Foote | 343/5 PD |
| 4,008,469 | 2/1977 | Chapman | 343/5 NA |
| 4,063,238 | 12/1977 | Conner, Jr. | 343/7.3 |
| 4,079,375 | 3/1978 | Tacussel | 343/5 PD |
| 4,197,537 | 4/1980 | Follen et al. | 343/5 PD |
| 4,210,912 | 7/1980 | Naidich et al. | 343/7.7 |
| 4,241,346 | 12/1980 | Watson | 343/7 A |
| 4,414,549 | 11/1983 | Wichmann | 343/18 E |
| 4,430,653 | 2/1984 | Coon et al. | 343/5 NA |
| 4,443,799 | 4/1984 | Rubin | 343/17.2 PC |
| 4,497,252 | 2/1985 | Taylor | 102/214 |
| 4,553,144 | 11/1985 | Houdard et al. | 343/7.7 |
| 4,565,996 | 1/1986 | Close | 340/572 |
| 4,596,023 | 6/1986 | Driver et al. | 375/55 |

(List continued on next page.)

FOREIGN PATENT DOCUMENTS

WO91/13370  5/1991  WIPO .............................. G01S 13/04

OTHER PUBLICATIONS

Scott, William B., "UWB Technologies Show Potential For High–Speed, Covert Communications", [*Aviation Week & Space Technology*], 40, 44, (Jun. 4, 1990).

Scott, William B., "Defense Dept. Panel of Radar Experts To Study Ultra–Wideband Technologies", [*Aviation Week & Space Technology*], 55, (Mar. 26, 1990).

Bennett, Leonard C. et al., "Time–Domain Electromagnetics and Its Applications" [*Proceedings of the IEEE*], 66, 3, 299–316 (Mar. 3, 1978).

Anderson, Forrest et al., "Wideband Beam Patterns From Sparse Arrays" [*Proceedings of the First Los Alamos Symposium*], 273–286.

Bretthorst, G. Larry, "Radar Target Discrimination Using Probability Theory" [*Proceedings of the First Los Alamos Symposium*], 417–434.

"Pulse and Waveform Generation with Step Recovery Diodes", Hewlett Packard Application Note 918, Hewlett–Packard, Jun. 1986, pp. 1–22.

*Primary Examiner*—John B. Sotomayor
*Attorney, Agent, or Firm*—Haynes & Beffel LLP

[57] ABSTRACT

A pulse Doppler radar motion sensor system and method for sensing target motion within a gated region is provided with approximately constant response versus target distance. The sensor includes a transmitter for transmitting a sequence of RF bursts comprised of a number of cycles at the transmitter frequency. The transmitted burst width alternates at a pattern frequency to provide a pattern of varying burst widths. The sensor includes a receiver responsive to the transmitted bursts and burst echoes from moving targets within its sensing field. The receiver produces a pattern frequency with a signal amplitude representative of the difference in moving target response for two different range gated regions defined by the transmitted burst widths. This difference is detected to provide a range invariant target motion response in a sharply defined region. Another mode provides a quadrature receive channel for target direction determination. Yet another mode time sequences the transmitted bursts to provide multiple range cell operation.

56 Claims, 8 Drawing Sheets

U.S. PATENT DOCUMENTS

| | | | |
|---|---|---|---|
| 4,641,317 | 2/1987 | Fullerton | 375/1 |
| 4,743,906 | 5/1988 | Fullerton | 342/27 |
| 4,816,833 | 3/1989 | Ferguson et al. | 342/95 |
| 4,875,198 | 10/1989 | Ariav | 367/93 |
| 4,905,008 | 2/1990 | Kawano et al. | 342/22 |
| 4,975,703 | 12/1990 | Delisle et al. | 342/21 |
| 4,979,186 | 12/1990 | Fullerton | 375/23 |
| 5,020,374 | 6/1991 | Petroff et al. | 73/861.25 |
| 5,084,706 | 1/1992 | Ross et al. | 342/368 |
| 5,226,328 | 7/1993 | Petroff et al. | 73/861.25 |
| 5,302,956 | 4/1994 | Asbury et al. | 342/70 |
| 5,333,508 | 8/1994 | Petroff et al. | 73/861.25 |
| 5,353,303 | 10/1994 | Walthall | 375/1 |
| 5,363,108 | 11/1994 | Fullerton | 342/27 |
| 5,420,589 | 5/1995 | Wells et al. | 342/22 |
| 5,455,593 | 10/1995 | Ross | 342/375 |
| 5,463,656 | 10/1995 | Polivka et al. | 375/200 |
| 5,521,600 | 5/1996 | McEwan | 342/27 |
| 5,573,012 | 11/1996 | McEwan | 128/782 |
| 5,576,627 | 11/1996 | McEwan | 324/639 |
| 5,581,256 | 12/1996 | McEwan | 342/27 |
| 5,586,145 | 12/1996 | Morgan et al. | 375/239 |
| 5,610,907 | 3/1997 | Barrett | 370/342 |
| 5,627,995 | 5/1997 | Miller et al. | 395/497.02 |
| 5,682,164 | 10/1997 | McEwan | 342/27 |
| 5,687,169 | 11/1997 | Fullerton | 370/324 |
| 5,844,481 | 12/1998 | Quintus et al. | 340/545.1 |

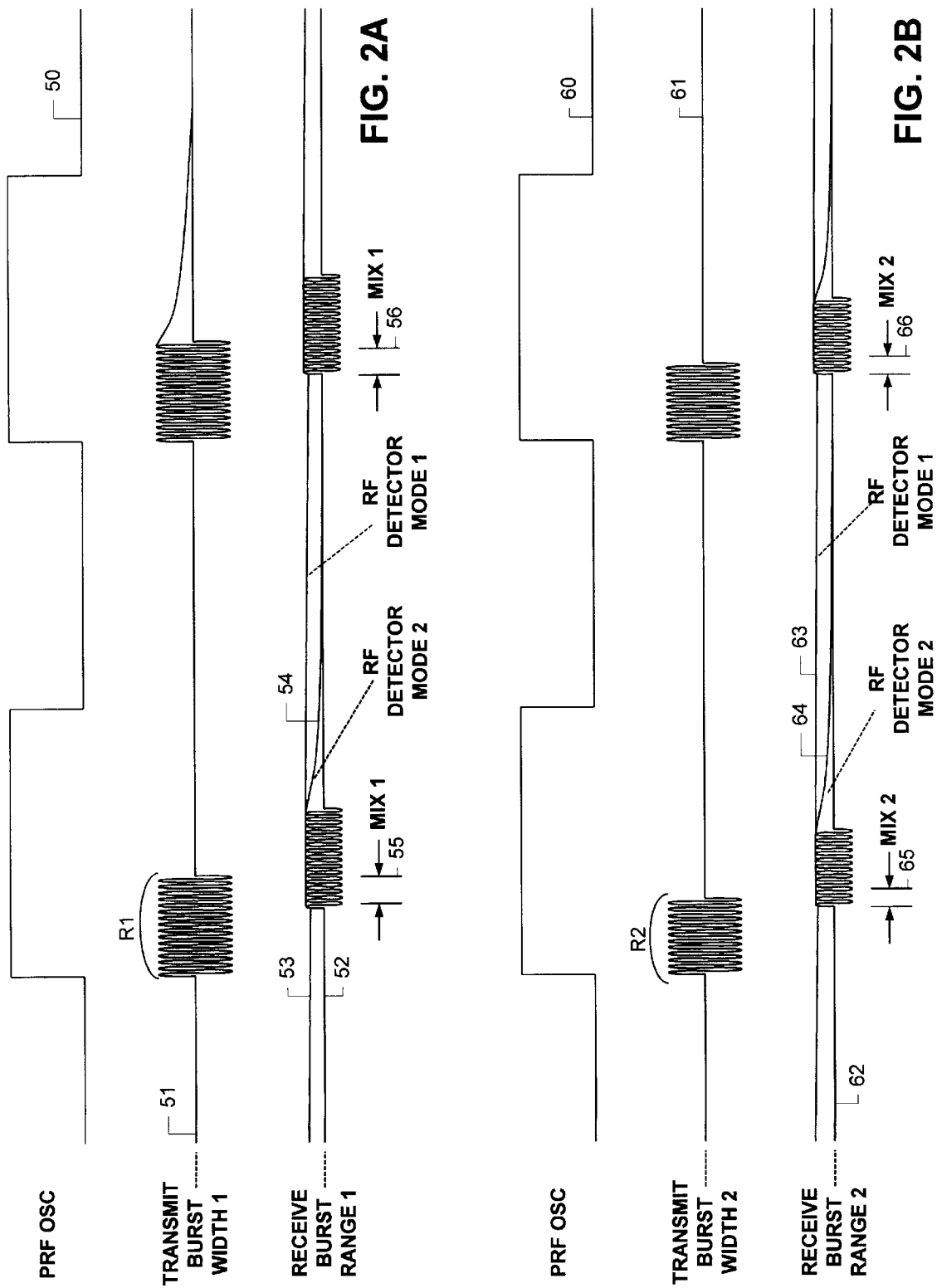

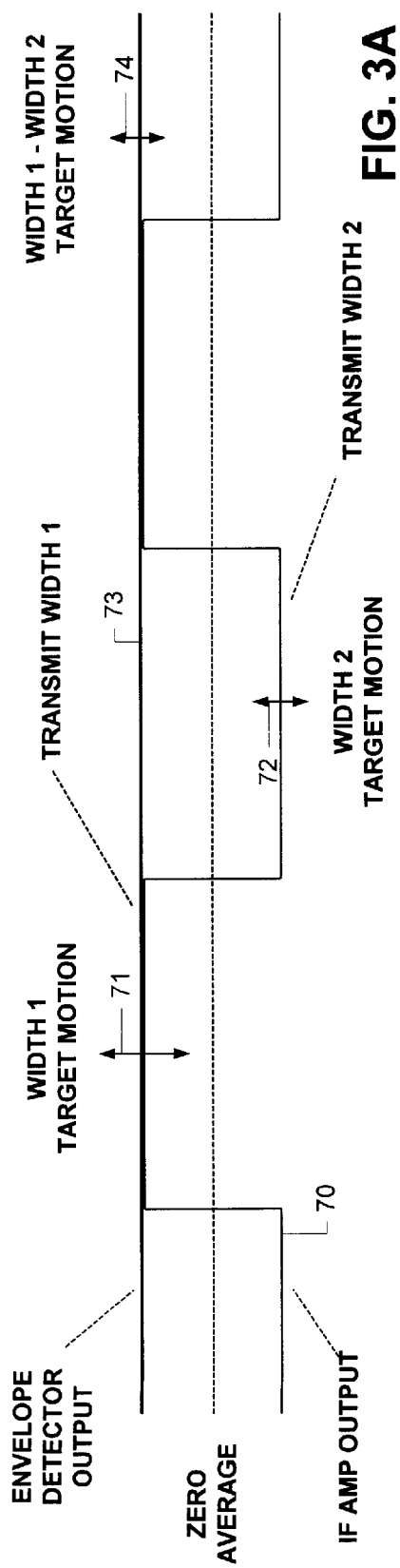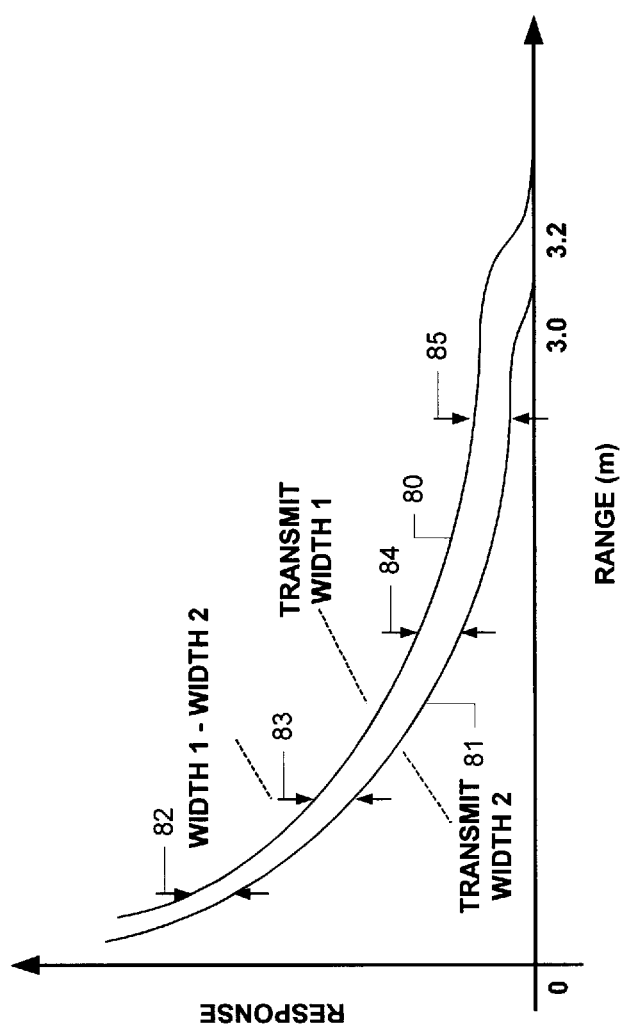
FIG. 3A
FIG. 3B

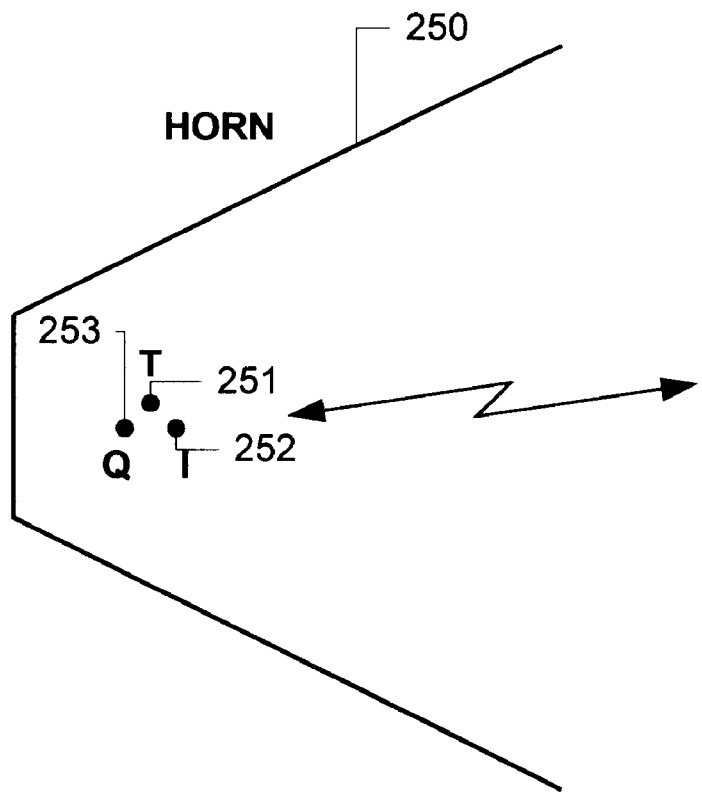
PLAN VIEW
SIDE VIEW
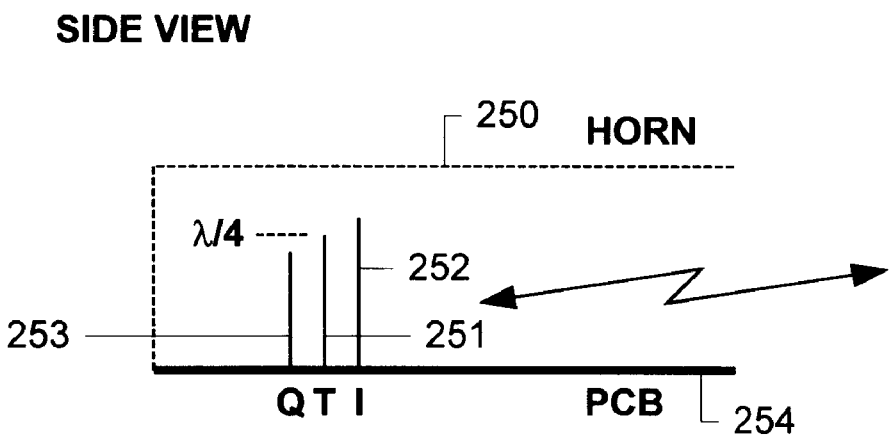
FIG. 7

DIFFERENTIAL PULSE RADAR MOTION SENSOR

BACKGROUND OF THE INVENTION

1. Field of the Invention

The present invention relates to electronic sensors, and more particularly to radar motion sensors based on pulse echo range gating.

2. Description of Related Art

Continuous Wave CW Doppler radar motion sensors emit a continuous wave, radio frequency RF carrier and mix the transmitted RF carrier with the return echos to produce a difference frequency equal to the Doppler shift produced by a moving target from which the carrier is reflected. CW Doppler sensors have a number of deficiencies that limit their wide spread application, including: 1) lack of a definite range limit, which leads to false triggers on distant clutter; 2) extremely high sensitivity at close range, causing false triggering on nearby small objects likes insects and on vibration; 3) high current consumption due to the CW operation making battery operation impractical; and 4) inability to co-locate sensors due to mutual interference.

Range limiting or gating of the Doppler radar can be implemented with either amplitude modulation AM or frequency modulation FM. In U.S. Pat. No. 3,719,944 by Adrian, a range limited FM Doppler proximity fuzing system for the U.S. Navy is disclosed. In this system, the range limit is related to FM bandwidth, and for short ranges of for example less than 3 meters, a high FM bandwidth, for example greater than 100 megaHertz is required. A main shortcoming with FM Doppler is response lobes that extend beyond the range limit. In other words, the range limit is not an absolute cut-off, just a substantial reduction in response. Another deficiency is the lack of range precision in low cost implementations. FM deviation in microstrip type oscillators is not well defined. In spite of these limitations, FM Doppler provides a response amplitude versus target distance that is much more uniform than seen in CW Doppler. The Adrian patent describes this technology in detail.

AM, or pulse, Doppler motion sensors have been described in U.S. Pat. No. 4,197,537 by Follen, et al., in U.S. Pat. No. 5,682,164 by McEwan, and others. In pulse Doppler, a short pulse is transmitted and its echo is mixed with either the transmitted pulse or a local oscillator such that either the pulse timing or its width defines the range gated region. With amplitude modulation, response beyond the gated region is zero because there is no leakage as in FM Doppler. While pulse Doppler exhibits excellent gating characteristics, its voltage response versus range varies with $1/R^2$, where R is equal to the range to the target. This $1/R^2$ characteristic occurs with CW Doppler as well. Thus a target at 10 meters range and a small object like an insect at 1 centimeter range may produce the same response. This problem with small objects and with nearby vibrations makes radar motion sensing too unreliable for many applications.

AM (pulse) and FM Doppler have been combined advantageously by Tresselt, U.S. Pat. No. 3,898,655, and by McEwan, U.S. Pat. No. 5,521,600. Pulse FM Doppler combines the best of both modulation techniques, resulting in zero response beyond range cutoff, and more uniform response within the gated region. The limitations with pulse FM Doppler include 1) difficulty in accurately controlling FM deviation, 2) an overly wide spectrum due to the combination of modulations, leading to regulatory constraints with for example the Federal Communication Commission FCC, and 3) the response within the gated region tends to vary with 1/R.

Accordingly there is a need for an improved radar motion sensor technology for commercial uses, and particularly for low power and short range applications.

SUMMARY OF THE INVENTION

The present invention provides a technique termed differential pulse Doppler motion sensor which solves many limitations of the prior art. The technique provides in a preferred embodiment a sensor with a range-invariant Doppler response within a range limited region, and no response outside the region. According to other aspects, the invention also provides a spread-spectrum microwave motion sensor that can be co-located with other spectrum users without having to set a specific operating frequency.

Accordingly, the present invention can be characterized as a sensor comprising a transmitter which transmits a sequence of transmitted bursts of electromagnetic energy to produce a sensor field, the transmitted bursts having burst widths which vary according to a pattern which cause responses to disturbance in the sensor field which also vary according to the pattern. For one example pattern, the transmitted bursts are switched between a first burst width and a second burst width at a pattern frequency. A receiver is included which receives a combination of the transmitted bursts and reflections of the transmitted bursts and produces a combined output. Thus, the combined output indicates a mixing of the transmitted burst with its own reflection. The width of the burst defines the range limit because any reflection which returns after the burst has ended, results in zero mixing. Signal processing resources are included which are responsive to the combined output and generate a sensor output signal indicating variations in differences in the combined output due to the pattern of varying burst widths. Thus according to the example mentioned above, the bursts having a first burst width will provide a combined output of a first amplitude while the bursts having the second burst widths will produce a combined output having a second amplitude. The difference between the first amplitude and the second amplitude will vary depending on disturbances in the sensor field.

According to another aspect of the invention, the transmitter transmits the sequence of transmitted bursts at a transmitter frequency with a burst repetition rate. The transmitter frequency is on the order of gigaHertz, such as between 900 megaHertz and 24 gigaHertz, or for example between about 5 and 6 gigaHertz. The burst repetition rate is on the order of megaHertz, such as for example 1–5 megaHertz, and more preferably 1–3 megaHertz. A burst width control circuit controls the pattern of varying burst widths by switching a burst widths of the transmitted bursts in the sequence between or among a plurality of burst widths according to a pattern. The pattern has for example a characteristic pattern frequency on the order of 10 kiloHertz to 100 kiloHertz. The pattern at which the burst widths are varied can take on a variety of characteristics. In a simple system, the burst widths are switched between two different burst widths. In other systems, a number of range cells are established by providing multiple pairs of burst widths, with each pair adapted for particular ranges, and by de-multiplexing the combined output of the receiver in order to detect motion within the particular range cells. In other embodiments, the pattern may vary according to a sine wave, a triangle wave, a ramp signal, or a noise modulated signal for example.

According to yet another aspect of the invention, the transmitter includes a radio frequency oscillator based on a bipolar or a FET transistor. The burst width control circuit is coupled to the emitter/source and collector/drain and starts a burst by lowering a voltage on the emitter/source of the transistor, and ends a burst by decreasing a voltage on the collector/drain of the transistor. A damping resistor is coupled to the collector/drain and a damping resistor is coupled to the emitter/source in a preferred example.

According to another aspect of the invention, the burst widths fall within a range of about 2 to 100 nanoseconds and the burst widths vary between about 1 nanosecond and 10 nanoseconds of a maximum burst width for a sequence of transmitted bursts within a particular range cell. Thus for example, a pattern of varying burst widths consists of a pattern of 12 nanosecond bursts and 14 nanosecond bursts at a burst repetition rate of 2 megaHertz, switching between the shorter burst width and the longer burst width at a pattern frequency of 20 kiloHertz. In this example with the 12 nanosecond/14 nanosecond burst width pattern is adapted for a range of about 3 meters.

According to other aspects of the invention, the receiver comprises a mixer which mixes a transmitted burst with reflections of the transmitted burst, combined with a pattern frequency filter to produce a pattern frequency signal. In another embodiment, the receiver includes a peak detector which detects a peak of a combination of a transmitted burst with reflections of the transmitted burst, along with a pattern frequency signal filter. The fall off time of the peak detector can be tuned to detect each peak, or to detect an average of many peaks depending on the particular application of the sensor desired.

According to other aspects of the invention, the signal processing resources of the sensor include an output filter which is adapted to detect differences in the pattern frequency signal according to the pattern of varying burst widths, in order to indicate motion in the sensor field. In one example, the output filter blocks frequencies below about 0.5 Hertz. The output filter can be adapted to detect vibration in the sensor field, such as for example vibration of guitar strings. In this example, the output filter is set to block frequencies below about 20 Hertz.

In other aspects of the invention, the receiver includes an in-phase channel and a quadrature phase channel. The signal processing resources in this example are used to determine the direction of motion in addition to the motion itself. In one embodiment including the in-phase and quadrature phase channels, the sensor includes a transmit antenna, an in-phase receive antenna and a quadrature phase antenna. In a preferred system, where the transmit frequency is above about 1 gigaHertz, an antenna horn is included having a focal point. The in-phase receive antenna and the quadrature phase receive antenna comprise antenna elements mounted at respective locations inside the horn within about $\lambda/8$, where $\lambda$ is the wavelength at the transmit frequency, of the focal point of the horn.

Thus, a preferred system has a duty cycle of about 1/100 and 1/10,000 providing for low power consumption and operation on batteries for long periods of time.

The present invention can also be characterized as a method for detecting disturbances in a field comprising transmitting a sequence of transmitted bursts of electromagnetic energy to produce a sensor field, where the transmitted bursts have burst widths which vary according to a pattern such as that described above. The method includes receiving a combination of transmitted bursts and reflections of the transmitted bursts and producing a combined output. Finally, the method includes processing the combined output to generate a sensor output signal indicating variations in differences in the combined output due to the pattern of varying burst widths.

The present invention also provides a sensor with a simplified, non-FM microwave oscillator that has suppressed spurious modes and a rapid turn-on and turn-off which allows for efficient production of high frequency bursts with varying burst widths. The sensor also allows for a reduced power consumption, high rejection of power supply variations, and low 1/F noise in the receiver. This invention can be applied to applications which require direction sensing capability, and provides for a novel quadrature antenna. Also, the motion sensor of the present invention can be applied to multiple range cell operation.

Overall the present invention provides a cost effective, low power and long lasting electronic sensor that is impervious to harsh environmental conditions such as dirt, rain, snow, acoustic noise, external thermal effects, and sunlight. Further the sensor of the present invention uses frequencies that can penetrate certain materials without damaging the material to allow users to install them behind the plastic panels, wood or concrete walls. Uses for the present invention include security alarms, home automation and lighting control, industrial and robotic controls, automatic toilet and faucet control, automatic door openers, vehicle backup warning and collision detection, and general appliance control.

Furthermore, the Doppler pass band of the present invention can be set to pass audio and higher frequencies making it responsive to vibrations. As a vibration sensor, the present invention can be used for industrial applications such as wheel and fan blade balancing. It can also be used for shaft vibration sensing, loud speaker sensing and control, guitar string and musical instrument pickup, and vocal cord vibration sensing.

In further embodiments, the present invention can be applied to body organ motion monitoring, such as cardiac motion monitoring, arterial pulse monitoring, and tongue motion.

Other aspects and advantages of the present invention can be seen upon review of the figures, the detailed description and the claims which follow.

BRIEF DESCRIPTION OF THE FIGURES

FIGS. 2A and 2B depict the transmit and receive timing relations for two different burst widths according to one example of the present invention.

FIGS. 3A and 3B illustrate the differential timing mechanism and its operational performance respectively.

FIG. 7 illustrates a plan view and side view of a quadrature antenna with co-located quadrature elements.

DETAILED DESCRIPTION

Figure 1:
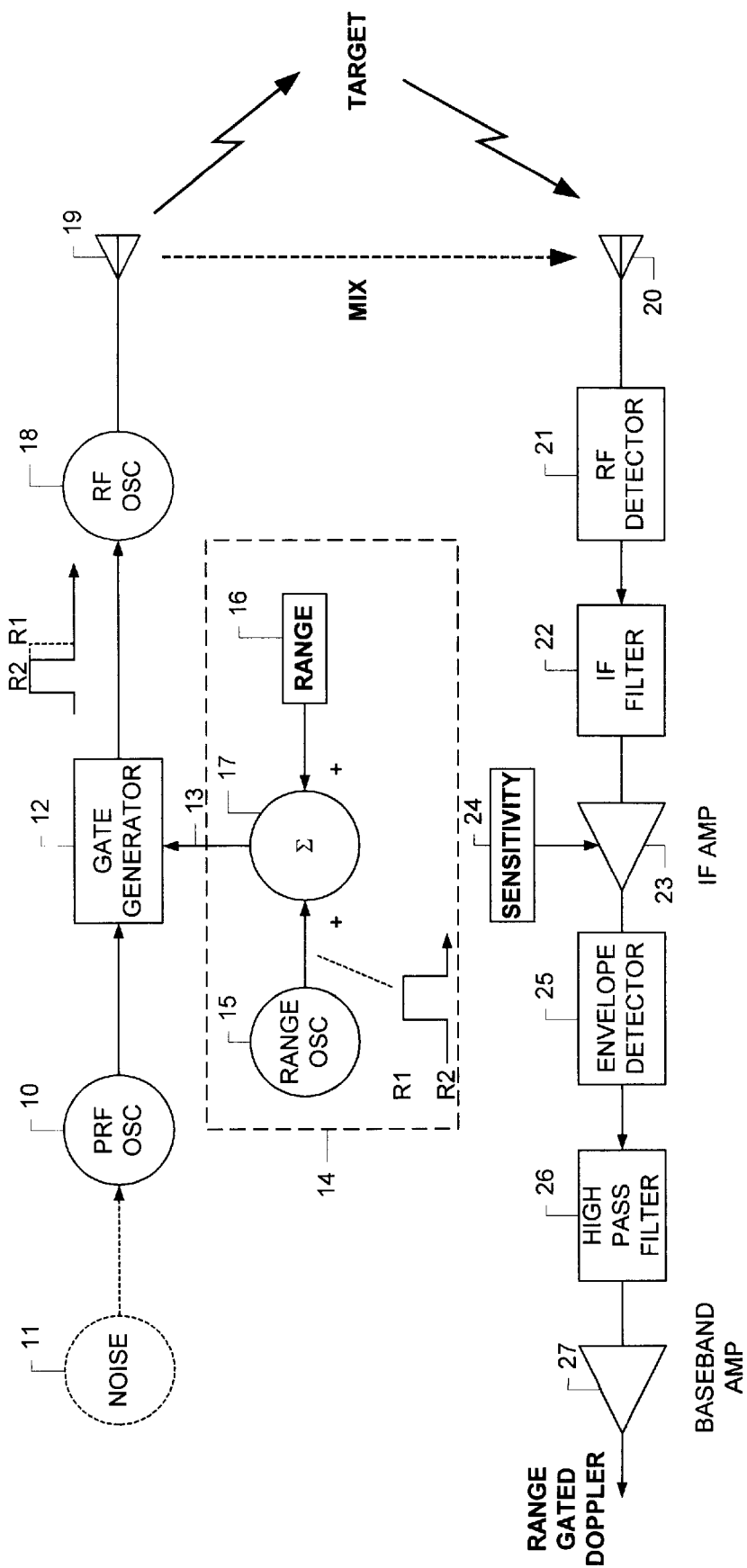
FIG. 1 is a block diagram of the differential pulse radar motion sensor of the present invention.

A detailed description of the present invention is provided with reference to the figures, in which FIG. 1 provides a block diagram of the motion sensor of the present invention. In FIG. 1, a pulse repetition frequency oscillator 10 provides a square wave pulse train at a pulse repetition rate of typically 1–10 megaHertz, and in this example about 2 megaHertz. The frequency of this oscillator may be noise modulated as indicated by the noise element 11, to spread the radiated spectral lines that would otherwise occur with the uniform spacing equal to the pulse repetition frequency. Noise modulation virtually eliminates the possibility of matching pulse repetition frequency interference from other sensors.

The pulse repetition frequency oscillator 10 drives a gate generator 12 to produce a pulse train of defined width, typically on the order of 2–100 nanoseconds. The gate generator has a control port which receives burst width control signals on line 13 to control the output widths. The burst width control signals are provided by a burst width control circuit generally 14 which in this example includes a range oscillator, a range setting potentiometer 16, and a summation node 17, which combines the effect of the oscillator and the potentiometer to produce the pulse width control signals on line 13. Alternative burst width control circuits include digital logic, program controlled processors, other analog approaches, and combination of the above. In this example, the range oscillator 15 typically oscillates between 10 kiloHertz and 100 kiloHertz, such as for example at 20 kiloHertz. It generates square waves to the burst width control port 13 through the summation node 17. This causes the gate generator 12 to vary its output pulse sequence between two pulse widths at a rate of the pattern frequency of the range oscillator, (20 kiloHertz). The range potentiometer 16 establishes the nominal pulse width for the gate generator, and thereby establishes the range. The pulses from the gate generator 12 turn on an RF oscillator 18 for the duration of the gate pulse. The oscillator typically generates a radio frequency burst on the order of gigaHertz, and preferably between 5 and 6 gigaHertz for burst widths having a duration of 2–100 nanoseconds, depending on the setting of the range potentiometer 16. The variation in pulse width provided by the gate generator in one example falls within 1 and 10 nanoseconds of the nominal maximum pulse width.

The RF oscillator 18 is connected to a $\lambda/4$ transmit monopole located at or near the focus of a horn antenna. In the present embodiment, the monopole and horn reside on a low cost printed circuit board and produce 8 dB gain at a transmitter frequency of 5.8 gigaHertz.

The antenna radiates the radio frequency bursts into a sensor field, and targets reflect back a portion of the RF energy. A $\lambda/4$ receive monopole 20 is co-located with the $\lambda/4$ transmit monopole inside the horn. The horn not only provides gain but also acts as a wave guide beyond cutoff for frequencies below about 3 gigaHertz, greatly reducing the chance of interference from cell phones or other microwave generators.

The receive monopole 20 provides a signal to an RF detector 21. The signal provided to the RF detector 21 is the sum of the transmitted RF burst and the reflection from a target of that burst. In a preferred embodiment, the RF detector detects the peak RF envelope and substantially holds the peak value from one burst to the next. However, the droop rate is such that it can follow the pattern frequency (20 kiloHertz) burst width variations established by the range oscillator 15.

The output of the RF detector 21 is passed through a pattern frequency filter 22 that is tuned to pass the burst width variation rate. Typically the pattern frequency filter comprises simply an RC high pass filter designed to reject DC offsets from the detector 21 and unmodulated, that is non-pattern frequency, Doppler variations. A pattern frequency amplifier 23, and a sensitivity adjustment potentiometer 24 provide user controllable gain before final detection. The sensitivity potentiometer 24 primarily effects the size of the target that is to be detected.

The output of the pattern frequency amplifier in this example provides a square wave oscillating at about the rate at which the bursts are varied (20 kiloHertz). It has a zero average value since it is passed through a high pass filter (pattern frequency filter 22) to remove the DC component. The high level of the square wave corresponds to a wide RF burst width and far range, amongst the burst widths of the transmitted sequence, and the low level of the square wave corresponds to a narrower RF burst width and a shorter range amongst the burst widths of the transmitted sequence. Due to the zero average condition, the peak of the square wave corresponds to the difference between the wide and narrow RF pulse levels. Thus, this combined output can be processed to detect variations in the differences between the response for the varying burst widths.

In this example, the output of the pattern frequency amplifier 23 is supplied to an envelope detector 25 where one of the high or low square wave levels can be peak detected, or envelope detected, to provide a resulting difference signal. The output of the envelope detector 25 corresponds to the difference in the radio frequency detector response between the two radio frequency burst widths, or between the two sensor ranges established by the varying burst widths.

The sensor range is defined by one-half of the radio frequency burst width. For echo detection to occur, the echo must return before the transmit pulse ends, otherwise there will be no mixing. The term mixing is used loosely here, in reality the echo burst adds or subtracts with a portion of the transmit burst, and the result is peak detected. A multiplying type mixer can be used, but peak rectifying detector is preferred for simplicity and high output.

The output of the envelope detector 25 is supplied to a high pass filter 26, where the signal is filtered to remove DC offsets. Typically the high pass corner frequency is about 0.5 Hertz for sensing human motion at 5.8 gigaHertz. The corner frequency is set for about 20 Hertz for sensing vibrations such as vibrations from guitar strings. The output of the high pass filter 26 is amplified by a base band operational amplifier 27. The output of the base band operational amplifier 27 provides range gated Doppler output which could be supplied to further analog signal processing circuits, threshold detected for alarm or lighting control, or converted to digital signals and processed in a variety of digital processing modes.

FIG. 2 depicts the timing relations while the range oscillator 15 is set for the wide burst width, that is R1 of FIG. 1. FIG. 2 provides the similar signals for the narrower burst width R2.

The upper trace 50 in FIG. 2A shows the 2 megaHertz pulse repetition frequency. The middle trace 51 provides the RF burst timing. The bottom trace 52 provides the receive burst timing. The burst width R1 is greatly exaggerated in this diagram for ease of understanding. In reality, the duty cycle of the bursts relative to the pulse repetition frequency falls in a range of about 1/100 to 1/1000. For a 2 megaHertz pulse repetition frequency and a 5 nanosecond pulse width, the duty cycle is 1/100.

Similarly, the receive burst amplitude is exaggerated. Also shown in the figure are a trace 53 and a trace 54 for the output of the RF detector 21 for two different modes. In the first mode, on trace 53 a long peak hold time is provided greatly exceeding the pulse repetition frequency pulse interval, but drooping enough to follow the 20 kiloHertz burst width variations. In a second mode, the RF detector output is illustrated at trace 54. In this example, a higher pattern frequency filtering can be utilized, which aids in rejecting oscillator noise. This may be preferable in systems using gallium arsenide FET oscillators due to their high 1/F noise corner. As can be seen, in the second mode at trace 54, the output of the RF detector 21 droops quickly so that it substantially reaches zero between the pulses.

In FIG. 2A, the overlap of the transmit burst and the receive burst is illustrated during the interval MIX 1 at 55 for a first burst and 56 for a second burst.

FIG. 2B illustrates the same signals for the range R2. Thus, the pulse repetition frequency is shown at 60, the transmit burst timing is provided at trace 61, and the receive burst timing is provided at trace 62. The RF detector output for mode 1 is provided at trace 63 and for mode 2 at trace 64. It can be seen that the overlap of the transmitted pulse and the received reflection is provided during the mixing interval MIX 2 at 65, for a first burst and MIX 2 at 66 for a second burst.

Variations in the difference between the MIX 1 regions 55, 56 and the MIX 2 regions 65, 66 are utilized to detect disturbance in the sensor field.

FIGS. 3A and 3B illustrate the differential timing mechanism and its operational performance respectively. FIG. 3A illustrates the output of the pattern frequency amplifier 22 on trace 70. The pattern frequency amplifier output 70 includes a first half cycle during which the burst width 1 target motion is reflected by the amplitude as indicated by the arrow 71. A second half cycle is provided during which the variation in the amplitude as indicated by the arrow 72 indicates the response for the second burst width. For a pattern of varying burst widths which switches between the one longer burst width and one shorter burst width at a pattern frequency, such as in this example, the square wave provided in FIG. 3A results.

Thus, the effective target motion for the RF burst width 1 and for the RF burst width 2 are provided at the upper and lower phases of the square wave. The output of the envelope detector 25 is provided at trace 73. In this example it is effectively clamped to the square wave positive level. Due to the zero average condition of the circuit, this amplitude represents the difference between the width 1 level 71 and the width 2 level 72. Thus, the envelope detector output provides a Doppler response difference between the two RF burst width conditions, or equivalently between the two different maximum range limits provided for this pattern of varying burst widths. The variations in the output of the envelope detector 25 is indicated by arrow 74 in FIG. 3A are utilized to detect target motion.

With reference to FIG. 3B, the performance of the sensor can be understood. FIG. 3B plots a first curve 80 for the first burst width, and a second curve 81 for the second burst width.

It can be seen that the response for the first burst width is larger than the response for the second burst width, and increases as the range decreases with a relation of about $1/R^2$. The response for the shorter second burst width also increases as the range decreases according to a similar function. However, it can be seen that the difference between the first burst width and the second burst width as indicated by the arrows 82, 83, 84 and 85 remains almost constant, even as the range approaches a zero range.

The Doppler response for a target at a particular range is stronger with a wider burst width. This occurs because the RF detector averages its response across the RF burst, and with a wider burst the Doppler mixing region becomes a higher fraction of the burst and thus produces a higher fluctuation.

Figure 4A:
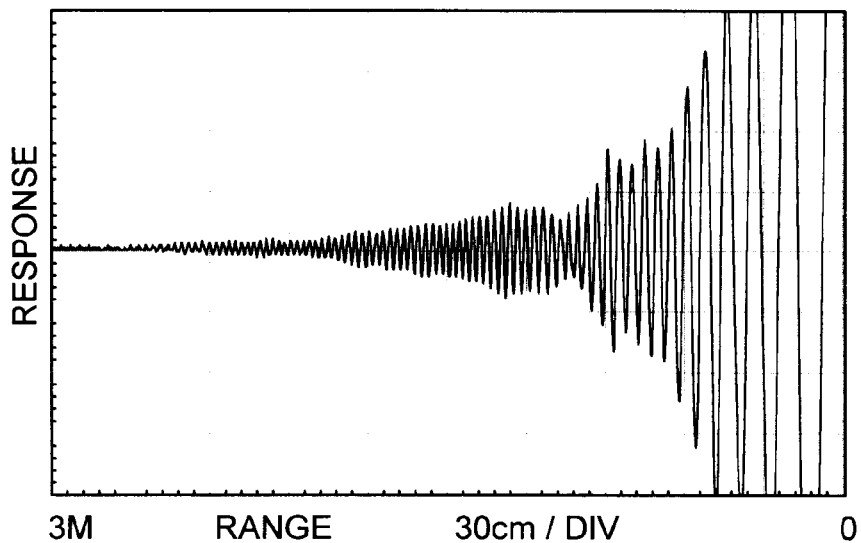
FIGS. 4A and 4B provide data without and with the differential pulse feature of the present invention.
Figure 4B:
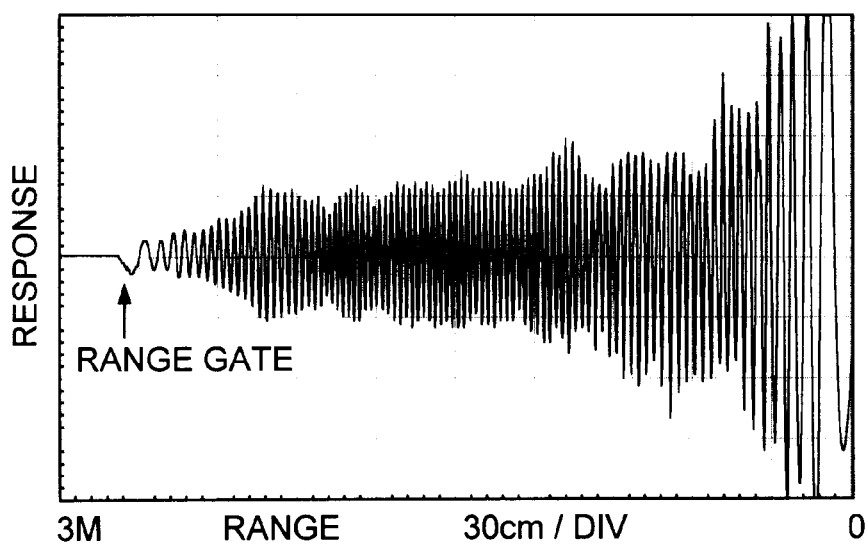

FIGS. 4A and 4B provide actual data without and with the differential pulse width feature of the present invention. FIG. 4A dramatically illustrates the major problem associated with virtually all prior art radar motion sensors. That is, its response varies 100 fold for a 10 fold change in range as the range is reduced. If the sensor is set to trigger on a distant target, it is usually sensitive to nearby objects. This $1/R^2$ effect makes CW Doppler sensors virtually useless for automotive applications where nearby structural vibrations are common, and for many other applications. Thus, as shown in FIG. 4A, using a constant transmit burst width, the response remains within a reasonable range until it falls inside about 60 centimeters in this example. Inside about 60 centimeters, the amplitude of the response goes off the charts.

In FIG. 4B, the response for the two burst width pattern is provided, showing substantially range invariant response. Response varies only a few dB for most of the range across the central portion of the plot. The variation at the left labeled "range gate" is a natural tail due to the range gate. A 10 dB increase in response can be seen at the right side of the plot, corresponding to a range of 30 centimeters or less. This unwanted increase may be due to non-linearities in the nonlinear detector or to near field effects. However, this response remains within a manageable limit providing for very short range applications of the present invention.

Figure 5:
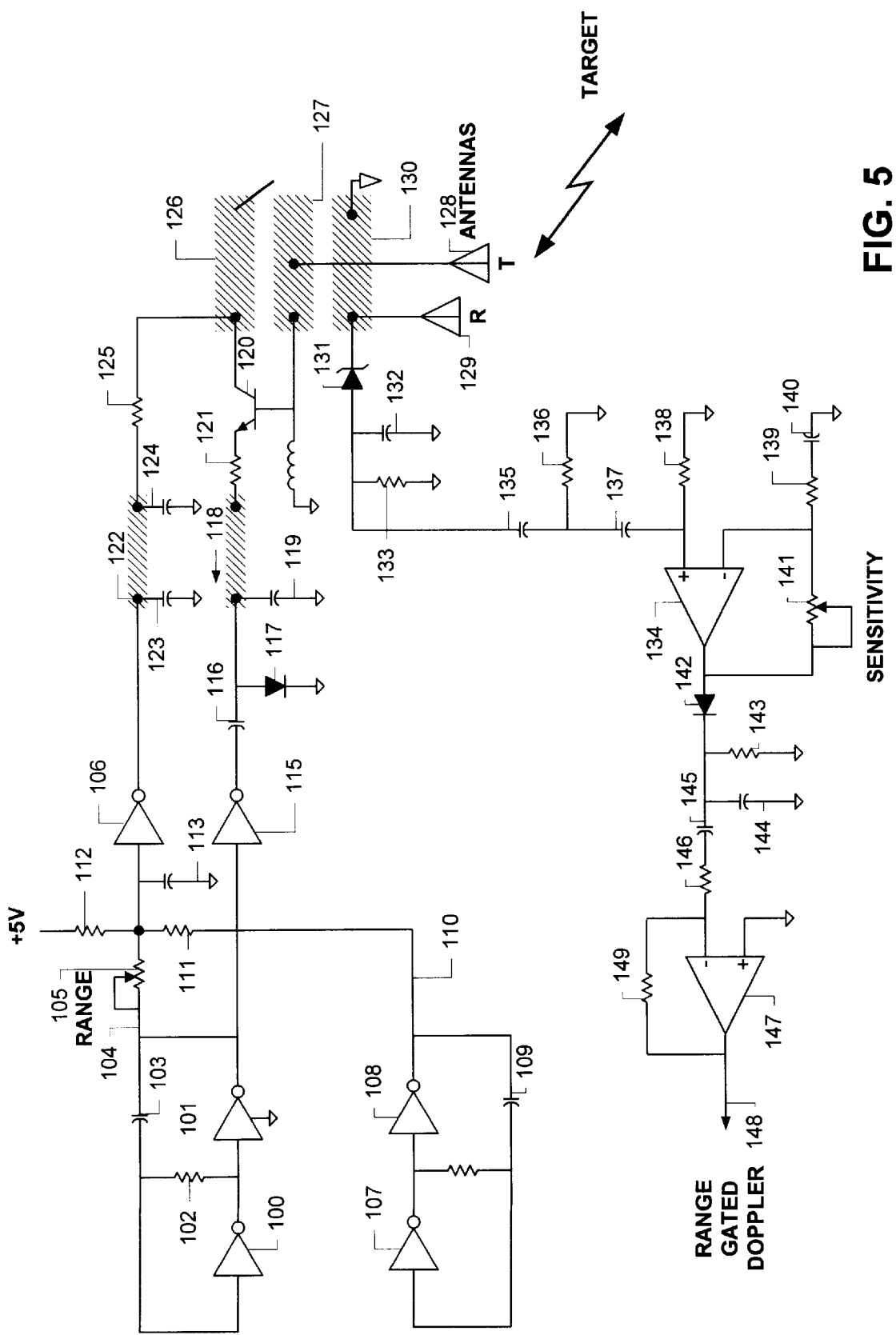
FIG. 5 provides a schematic diagram of a preferred embodiment of the invention.

FIG. 5 is a schematic diagram of one preferred embodiment of the present invention. The circuit includes a pulse repetition frequency oscillator composed of inverter 100 and inverter 101 connected in series. Resistor 102 and capacitor 103 are connected in a feedback loop from the output of inverter 101 to the input of inverter 101. Also, the node between the resistor 102 and the capacitor 103 is connected to the input of inverter 100. This produces a 2 megaHertz pulse repetition frequency signal on node 104.

A potentiometer 105 is connected between node 104 and the input of inverter 106. A pattern frequency oscillator composed of invertors 107 and 108, having capacitor 109 connected in feedback between the output of inverter 108 and the input of inverter 107, and a resistor 110 connected between the output of inverter 107 and the input of inverter 107 are included. This establishes a square wave at node 110 which switches at approximately 20 kiloHertz to provide for the variation in pulse width. The signal at node 110 is supplied through a resistor 111 to the input of inverter 106. Resistor 112 is connected between the input of inverter 106 and the power supply. Also a capacitor 113 is connected from the input of inverter 106 and ground.

A range gate generator includes inverter 106 and inverter 115. The inverter 106 drives an upper path of the range gate. The inverter 115 drives a lower path. The lower path through inverter 115 is connected through capacitor 116 to the anode of diode 117. The cathode of diode 117 is connected to ground. Also the anode of diode 117 is connected to a microstrip tuning element 118, and across capacitor 119 to ground. This circuit acts as a capacitive level shift network. This shifts the 0 to 5 volts square wave at the output of the inverter 115 to a 0.7 volt to −4.3 volt square wave on the microstrip 118. The negative level of the square wave on the microstrip 118 biases the RF oscillator in the on condition by pulling the emitter of transistor 120 low through a damping resistor 121.

The upper path of the gate generator is driven through inverter 106. The input to the inverter 106 is driven through a variable delay induced by the burst width control signals at the input provided by the range potentiometer 105, and the pattern frequency oscillator signal on line 110. As a result, a variable delay is introduced into the upper path. If the range gate is set for 2 meters range, the upper path square wave will be delayed about 13 nanoseconds relative to the lower path, corresponding to the round trip propagation delay to and from the target. The action of the 20 kilohertz square wave is to toggle this delay between about 12 and 14 nanoseconds for example. Accordingly, the RF burst width is made to alternate between these two widths at a 20 kiloHertz rate.

The output of the inverter 106 is connected to a microstrip decoupling element 122, and across capacitor 123 to ground. The decoupling element is coupled at the opposite end across capacitor 124 to ground, and through a damping resistor 125 to the collector of the oscillator transistor 120. This path provides a 5 volt to 0 volt transition shortly after the lower path biases the RF oscillator on. Once the upper path goes to 0 volts, the RF oscillator provided by the transistor 120 very quickly ceases to oscillate having lost power. Further, residual ringing and oscillations are quickly damped by collector-base diode conduction, and high junction capacitance at 0 bias. In practice, a low cost silicon bipolar transistor 120 in a SOT-23 package turns on and off with approximately 1 nanosecond RF envelope transition times at 5.8 gigaHertz. Alternative systems include MOS transistors or GaAs FET transistor, in place of transistor 120. The use of the two path, gate generator provides for matched inverter delays and can produce very small RF burst widths since the difference between two separate timing agents is relied on, and not the minimum pulse width that can be propagated through a single inverter, as would be the case for the single drive line to the RF oscillator.

The RF oscillator is a tuned-base, tuned-collector type oscillator using $\lambda/4$ microstrip elements 126 and 127 connected to the collector and base respectively. The microstrips 126, 127 are coupled at their ends with small capacitance that enhances oscillation and provides a means for fine tuning. (Capacitance not shown). A key feature of this oscillator is the incorporation of resistors 125 and 121 on the order of 100 ohms into the collector and emitter legs. After extensive experimentation it was found to produce a fist start oscillator that did not exhibit frequency chirp nor pronounced waveform shifts right after startup. The addition of the resistors eliminated these aberrations. A transmit $\lambda/4$ monopole antenna 128 is tapped onto one of the microstrips, either the base microstrip 127 or the collector microstrip 126. In this example, the base microstrip 127 is preferred. In near proximity, about $\lambda/8$, a receive $\lambda/4$ monopole 129 is situated, and coupled to a $\lambda/4$ microstrip resonator 130. The resonator 130 drives a Schottky detector diode 131. Typically about 1 volt of radio frequency energy is present during the transmit bursts, and these bursts are peak detected as shown in FIGS. 2A and 2B. A capacitor 132 and a resistor 133 are connected from the anode of the diode 131 to ground. The values of these devices set the peak hold characteristics. In an alternative embodiment, a radio frequency mixer could be utilized.

The RF peak hold output at the anode of the diode 131 is coupled to a pattern frequency amplifier 134 through a high pass filter comprising a capacitor 135 connected to the anode of diode 131 on one side, and across resistor 136 to ground on the second side. Also, the second side of the capacitor 135 is connected through capacitor 137 to the input of the amplifier 134. Also the input of the amplifier is connected across resistor 138 to ground. In this example, the high pass filter is connected to the positive input of the differential amplifier 134. The negative input of the differential amplifier 134 is connected across resistor 139 and capacitor 140 to ground. Also a sensitivity potentiometer 141 is connected from the output of the amplifier 134 in feedback to the negative input. The high pass filter passes the pattern frequency modulated signal, but rejects DC detector bias, low frequency Doppler modulation, that is non-range differenced Doppler, detector 1/F noise, which may be substantial with gallium arsenide FET transmitter oscillators, and power supply glitches induced onto the detector bias level. If the RF peak detector is set to droop substantially at the pulse repetition frequency rate, then the pattern frequency filter can be set to 2 megaHertz rather than 20 kiloHertz. This provides substantial improvement in the above mentioned properties of noise rejection. However, using the silicon bipolar transmit oscillator mentioned above, little improvement is seen in practice, and the 20 kilohertz pattern frequency filter allows the use of a lower bandwidth pattern frequency amplifier 134.

The pattern frequency amplifier gain is set by the sensitivity potentiometer 141. This sets overall receiver gain and defines the trip level of an alarm or other circuit when the receiver output is coupled to a threshold detector.

The pattern frequency amplifier 134 is connected to a simple diode-capacitor peak detector, by connecting the output of the amplifier 134 to the anode of a diode 142. The cathode of the diode 142 is connected across resistor 143 to ground and across capacitor 144 to ground. Also, it is connected through capacitor 145 and resistor 146 to the input of an output amplifier 147. The peak detector detects the square or sine wave that results from the difference in signals from the first burst width and the second burst width. Alternatively, an analog switch may be utilized instead of a peak detector, where the switch control can be connected to the range oscillator (e.g. at node 110) providing a synchronous rectifier type output.

The output of the peak detector provides a DC level that varies in amplitude with a Doppler signal representative of the Doppler differences between the two burst widths. The DC level is removed with a coupling capacitor 145, and the final Doppler output is amplified by a baseband amplifier 147 to a desired level. The level of the output 148 is set by the feedback resistor 149 relative to the impedance on the input of the amplifier 147 as known in the art. The positive input to the amplifier 147 is coupled to ground in this example.

Figure 6:
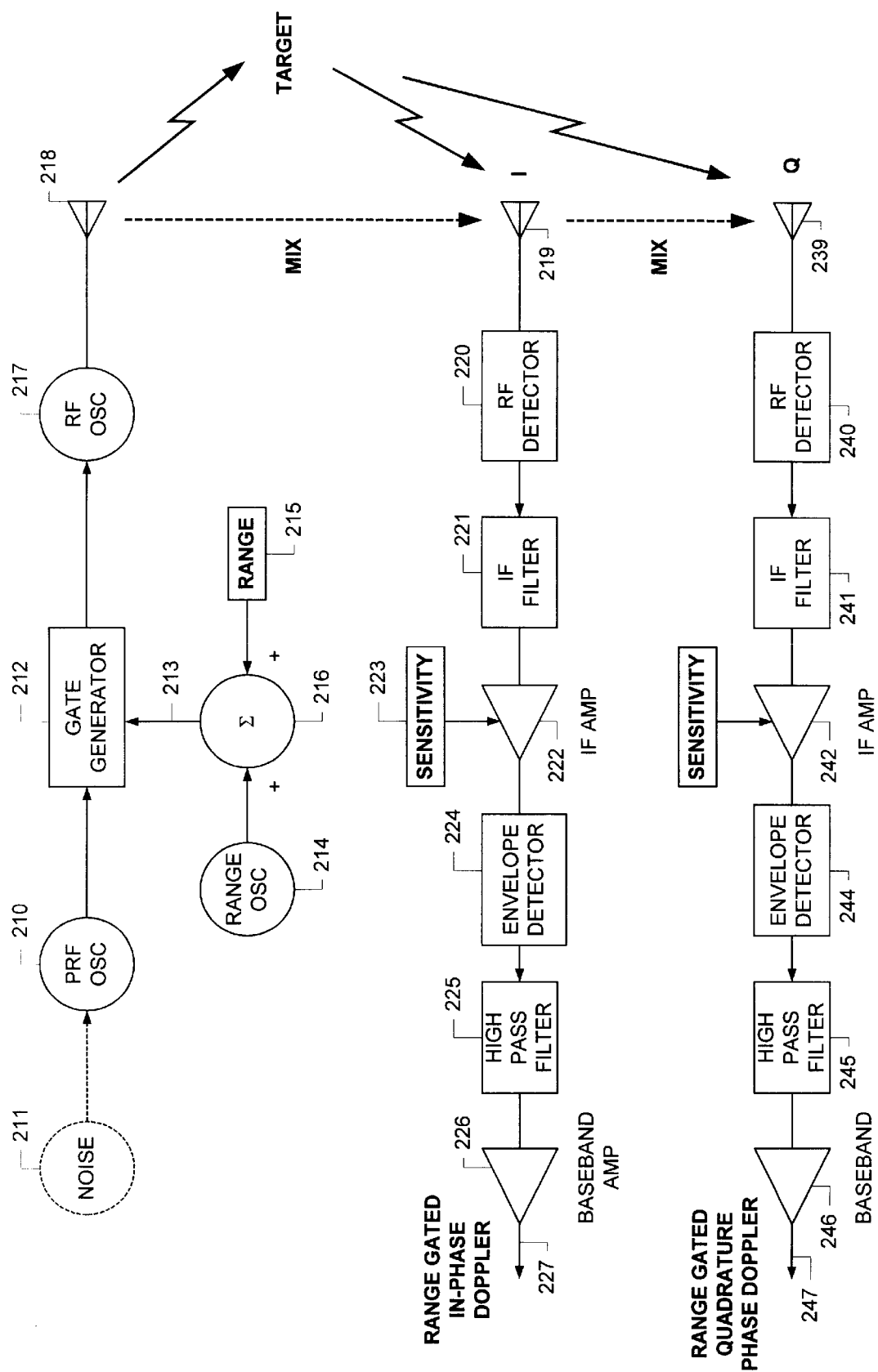
FIG. 6 provides a block diagram of an embodiment of the invention with quadrature Doppler channels.

FIG. 6 provides a block diagram of an embodiment of the invention with quadrature Doppler channels. In FIG. 6, the transmitter is essentially the same as that in FIG. 1. Thus it includes a pulse repetition frequency oscillator 210 which may be modulated by a noise source 211. The output of the pulse repetition frequency oscillator 210 is supplied to a gate generator 212 and RF oscillator 217 which generates a sequence of transmitted bursts having varying burst widths according to a pattern determined by the burst width control signals on lines 213. The burst width control signals on line 213 are supplied by a range oscillator 214 and a range potentiometer 215 in this example which are summed at node 216 and supplied on line 213 to the gate generator 212. The output of the gate generator 212 is supplied to a transmitter oscillator 217 which is coupled to a transmit antenna 218.

The quadrature channels consist of parallel receivers similar to the receiver illustrated in FIG. 1. Thus, an in-phase channel includes an in-phase receive antenna 219 which is connected to an RF detector 220. The output of the detector is supplied through a pattern frequency filter 221. The output of the filter 221 is supplied through a pattern frequency amplifier 222 which has a sensitivity control circuit 223. The output of the pattern frequency amplifier 222 is supplied through an envelope detector 224 and a high pass filter 225. The output of the high pass filter is supplied through a baseband amplifier 226 to supply the range gated in-phase Doppler signal on line 227. A quadrature channel has a quadrature antenna 239 coupled to a radio frequency detector 240. The output of the detector 240 is supplied to a pattern frequency filter 241 which drives a pattern frequency amplifier 242 having sensitivity control circuit 243. An envelope detector 244 receives the output of the pattern frequency amplifier and drives a high pass filter 245. The output of the filter 245 is supplied to a base band amplifier 246 which supplies a range gated quadrature phase Doppler signal on line 247. The in-phase and quadrature phase Doppler signals can be processed in further signal processing resources to determine target motion, and the direction of such motion.

FIG. 7 illustrates the monopole and horn geometry of a preferred embodiment of the present invention for use with the quadrature channels of FIG. 6. Thus, the horn plan view includes a reflector 250, a transmit monopole 251, an in-phase receive monopole 252, and a quadrature phase receive monopole 253. The three monopoles are co-located at or near the focus of the horn, preferably within about $\lambda/8$ of the focus of the horn. To achieve quadrature relation between the in-phase and quadrature phase monopoles 252, 253, one has a length cut slightly below resonance and the other has a length cut slightly above resonance as indicated by the side view of the horn. This provides a 90 degrees phase relationship for the monopoles. Experiments show that this tight physical arrangement provides direction sensing capability similar to that provided by separated in-phase and quadrature phase antennas. The horn reflector 250 is mounted on a printed circuit board 254 as can be seen in the side view in FIG. 7.

A primary purpose for quadrature channels is to determine direction, since the phase relationship between the in-phase and quadrature channels is a function of target direction. It is common practice to threshold detect the in-phase and quadrature phase channels and to apply the results to the clock and D inputs of a flip flop. The output state of the flip flop will then indicate target direction.

The in-phase and quadrature phase channels are implemented in FIG. 6 as a simple copy of the system shown in FIG. 1 with a second receiver channel. The monopole receive antennas provide 90 degrees radio frequency phase difference to their respective detector diodes. In conventional practice the in-phase and quadrature phase antennas are physically separated by $\lambda/4$ along the range direction. However, this is not practical where the antennas need to be located at the focus of a horn antenna. Locating one of the quadrature antennas $\lambda/4$ away from the focus results in degraded gain and directional properties. Thus, the antenna provided by the embodiment of FIG. 7 provides for substantially co-located antennas to generate quadrature outputs in a horn antenna.

Figure 8:
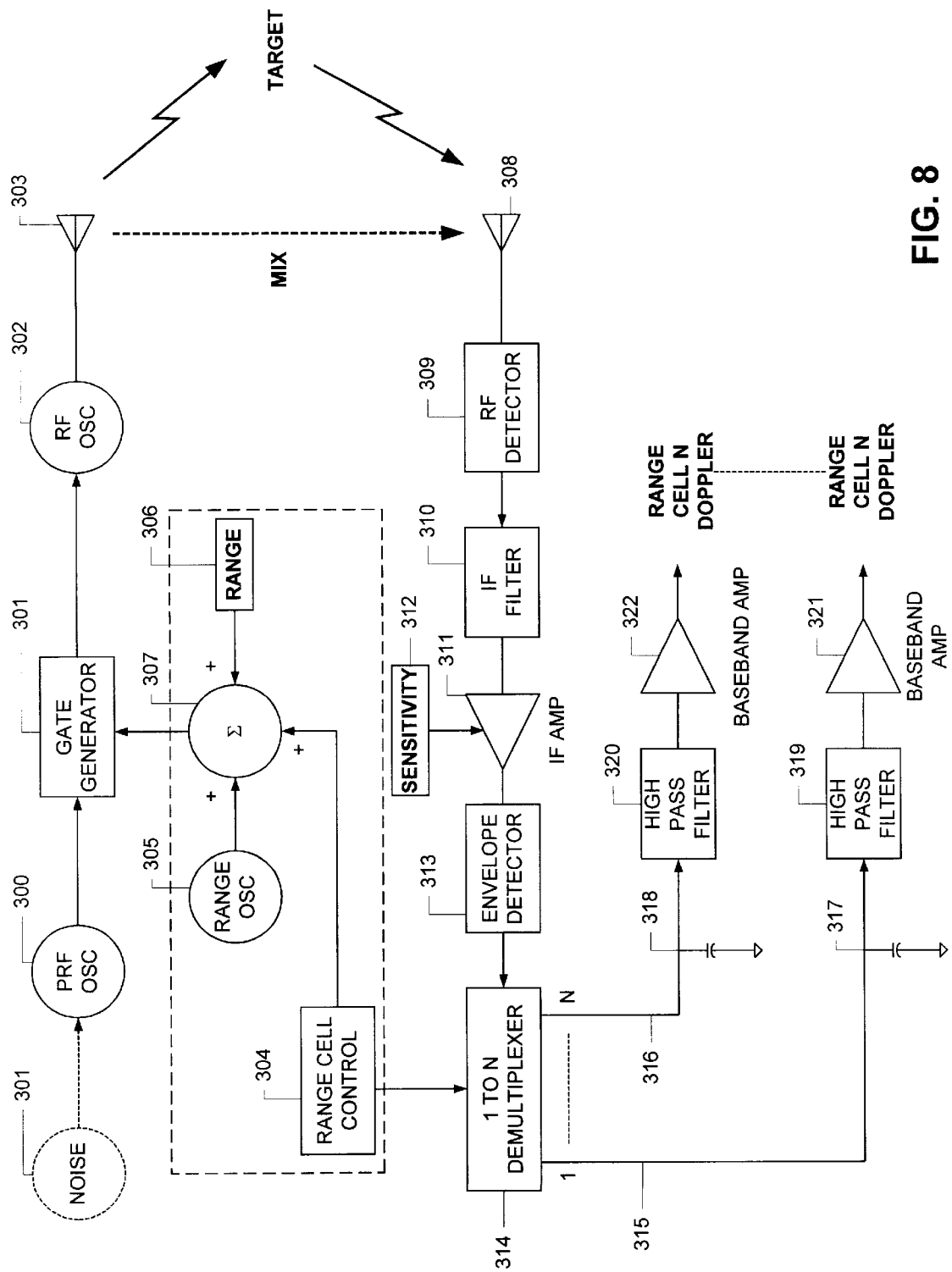
FIG. 8 is a block diagram of an embodiment of the invention with multiple range cells.

FIG. 8 is the block diagram of an embodiment of the present invention adapted for multiple range cells. It is often desirable to provide a number of parallel receiver channels each responsive to targets in different zones and range cells. Thus, multiple range cells can be implemented with multiple copies of the system of FIG. 1, each set to a different range. Alternatively, as illustrated in FIG. 8, a single system can have its range control time-hopped among a number of discreet range locations.

Thus in the embodiment of FIG. 8, a transmitter is comprised of a pulse repetition frequency oscillator 300, which may be noise modulated as indicated by the block 301. The output of the pulse repetition frequency oscillator 300 is supplied to a gate generator 301 which drives a RF oscillator 302 through which varying burst widths are applied to the transmit antenna 303. The burst width control circuitry in this example is expanded to include a range cell control block 304. Thus, a range oscillator 305 and a range potentiometer 306 are summed at node 307 with the output of range cell control block 304. This results in a pattern of varying burst widths with discreet pairs of burst widths set for each range cell desired to be detected.

Receive antenna 308 drives an RF detector 309 and a pattern frequency filter 310 as before. The output of the pattern frequency filter 310 is supplied to a pattern frequency amplifier 311 which has a sensitivity control 312. An envelope detector 313 is coupled to the output of the pattern frequency amplifier 311. The output of the envelope detector in this example is supplied to a demultiplexer 314 which is coupled to the range cell control block 304. The demultiplexer 314 drives a plurality of outputs 315-316. Each output includes a sample holding capacitor 317, 318, which is coupled to a high pass filter 319-320. The high pass filter 319 drives a base band amplifier 321, and the high pass filter 320 drives a base band amplifier 322, which provide for the range cell outputs for the respective cells. The demultiplexer 314 is controlled by the range cell control block 304 to hop between range cells in coordination with the pattern of varying burst widths generated by the transmitter.

Accordingly, a range cell control block 304 can be utilized as shown in FIG. 8. Typically, the range cell control block can be implemented using a counter and a digital/analog converter to provide range control to the gate generator. In the receive path, the demultiplexer steers the Doppler signal from the envelope detector into multiple parallel base band paths, such that for each range setting provided by the range cell control block, there is a corresponding demultiplexed base band Doppler channel.

The range cell control can step through each range at a very slow rate to check for activity in each cell, or preferably it steps at a rate well above the Doppler frequencies. At the high stepping rate, capacitors connected to the demultiplexer, that is capacitors 317, 318, serve as holding capacitors to store the instantaneous Doppler level between revisits of the multiplexer. This eliminates a spectral line at the range cells stepping rate and makes base band outputs appear as steady full parallel channels.

Accordingly, the present invention provides substantially improved radar motion sensor which overcomes many of the problems with prior art systems, and can be utilized in a wide variety of settings. This system is particularly suited to short range settings and low power applications.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A sensor comprising:
   a transmitter which transmits a sequence of transmitted bursts of electromagnetic energy to produce a sensor field, the transmitted bursts having burst widths which vary according to a pattern;
   a receiver which receives a combination of the transmitted bursts and reflections of the transmitted bursts and produces a combined output; and
   signal processing resources responsive the combined output which generate a sensor output signal indicating variations in differences in the combined output due to the pattern of varying burst widths.

2. The sensor of claim 1, wherein the transmitter includes:
   a burst width control circuit which controls the pattern of varying burst widths, by switching the burst widths of the transmitted bursts in the sequence of transmitted bursts between a first burst width and a second burst width at a pattern frequency.

3. The sensor of claim 1, wherein the transmitter includes:
   a burst width control circuit which controls the pattern of varying burst widths, by switching the burst widths of the transmitted bursts in the sequence of transmitted bursts between or among a plurality of burst widths according to the pattern.

4. The sensor of claim 1, including a circuit coupled to the transmitter by which to adjust the burst width.

5. The sensor of claim 1, wherein the transmitter transmits the sequence of transmitted bursts at a transmitter frequency with a burst repetition rate, and the transmitter frequency is on the order of gigaHertz and the burst repetition rate is on the order of megaHertz.

6. The sensor of claim 1, wherein the transmitter includes a transmit antenna and the receiver includes a receive antenna, and the transmit and receive antennas are mounted such that the transmitted bursts are proximity coupled to the receive antenna.

7. The sensor of claim 1, wherein the transmitter includes:
   a radio frequency oscillator responsive to burst width control signals to produce the transmitted bursts, and
   a burst width control circuit, coupled to the oscillator, which generates the burst width control signals to vary the burst widths of the transmitted bursts in the sequence of transmitted bursts according to the pattern.

8. The sensor of claim 7, wherein the pattern comprises switching between a first burst width and a second burst width at a pattern frequency.

9. The sensor of claim 7, wherein the pattern comprises varying the pulse width in response to a substantially continuously varying control signal.

10. The sensor of claim 9, wherein the substantially continuously varying control signal comprises a sine wave at a pattern frequency.

11. The sensor of claim 9, wherein the substantially continuously varying control signal comprises a triangle wave at a pattern frequency.

12. The sensor of claim 9, wherein the substantially continuously varying control signal comprises a ramp signal at a pattern frequency.

13. The sensor of claim 9, wherein the substantially continuously varying control signal comprises a noise modulated signal at a pattern frequency.

14. The sensor of claim 1, wherein the transmitter comprises an oscillator including a transistor having a source, a gate and a drain, and
   a burst width control circuit coupled to the source and drain, which starts a burst by lowering a voltage on the source of the transistor, and a ends a burst by decreasing voltage on the drain of the transistor.

15. The sensor of claim 14, including a damping resistor coupled to the drain of the transistor.

16. The sensor of claim 14, including a damping resistor coupled to the source of the transistor.

17. The sensor of claim 1, wherein the transmitter comprises an oscillator including a transistor having an emitter, a base and a collector, and
   a burst width control circuit coupled to the source and drain, which starts a burst by lowering a voltage on the emitter of the transistor, and ends a burst by decreasing voltage on the collector of the transistor.

18. The sensor of claim 17, including a damping resistor coupled to the collector of the transistor.

19. The sensor of claim 17, including a damping resistor coupled to the emitter of the transistor.

20. The sensor of claim 1, wherein the transmitter comprises:
   a radio frequency oscillator having a transmit frequency between 900 megaHertz and 24 gigaHertz.

21. The sensor of claim 1, wherein the transmitter comprises:
   a radio frequency oscillator having a transmit frequency between 5 and 6 gigaHertz.

22. The sensor of claim 1, wherein the burst widths fall within a range from about 2 to 100 nanoseconds, and the burst widths vary between about 1 and 10 nanoseconds of a maximum burst width for the sequence of transmitted bursts.

23. The sensor of claim 1, wherein the burst widths fall within a range from about 2 to 20 nanoseconds, and the burst widths vary between about 1 and 10 nanoseconds of a maximum burst width for the sequence of transmitted bursts.

24. The sensor of claim 1, wherein the burst widths vary between about 10 percent and about 50 percent of a maximum burst width for the sequence of transmitted bursts.

25. The sensor of claim 1, wherein the pattern is characterized by a pattern frequency and receiver includes:
   a mixer which mixes a transmitted burst with reflections of the transmitted burst, and a pattern frequency filter, coupled to the mixer, to produce a pattern frequency signal.

26. The sensor of claim 1, wherein the receiver includes:
   a peak detector which detects a peak of a combination of a transmitted burst with reflections of the transmitted burst, and a pattern frequency filter, coupled to the peak detector, to produce a pattern frequency signal.

27. The sensor of claim 1, wherein the signal processing resources comprise:
   an output filter adapted to detect differences in the combined output of the receiver according to the pattern which indicate motion in the sensor field.

28. The sensor of claim 27, wherein the output filter blocks frequencies below about 0.5 Hertz.

29. The sensor of claim 27, wherein the signal processing resources comprise:
   an output filter adapted to detect differences in the pattern frequency signal according to the pattern which indicate vibration in the sensor field.

30. The sensor of claim 29, wherein the output filter blocks frequencies below about 20 Hertz.

31. The sensor of claim 1, wherein the receiver includes an in-phase channel and a quadrature phase channel.

32. The sensor of claim 31, including a transmit antenna, an in-phase receive antenna and a quadrature phase receive antenna.

33. The sensor of claim 32, wherein the transmitted bursts have a transmit frequency above about 1 gigaHertz, and including an antenna horn having a focal point, and wherein the in-phase receive antenna and the quadrature phase receive antenna comprise antenna elements mounted at respective locations inside the horn, within about lambda/8 at the transmit frequency of the focal point of the horn.

34. The sensor of claim 1, wherein the pattern establishes a plurality of range cells, and the signal processing resources demultiplex the combined output to provide sensor output signals for the plurality of range cells.

35. A sensor comprising:
a transmitter which transmits a sequence of transmitted bursts of electromagnetic energy to produce a sensor field, the transmitter including
a radio frequency oscillator responsive to burst width control signals to produce the transmitted bursts having a transmitter frequency between about 900 megaHertz and 24 gigaHertz, and
a burst width control circuit, coupled to the oscillator, which generates the burst width control signals to vary the burst widths of the transmitted bursts in the sequence of transmitted bursts according to a pattern, the transmitted bursts having burst widths in a range of about 2 to 100 nanoseconds;
a receiver which receives a combination of the transmitted bursts and reflections of the transmitted bursts and produces a combined output; and
signal processing resources responsive the combined output which generate a sensor output signal indicating motion in the sensor field indicated by differences in the combined output due to the pattern of varying burst widths.

36. The sensor of claim 35, wherein the pattern comprises switching between a first burst width and a second burst width at a pattern frequency.

37. The sensor of claim 35, wherein the pattern is characterized by a pattern frequency and receiver includes:
a mixer which mixes a transmitted burst with reflections of the transmitted burst, and a pattern frequency filter, coupled to the mixer, to produce a pattern frequency signal.

38. The sensor of claim 35, wherein the receiver includes:
a peak detector which detects a peak of a combination of a transmitted burst with reflections of the transmitted burst, and a pattern frequency filter, coupled to the peak detector, to produce a pattern frequency signal.

39. The sensor of claim 35, wherein the signal processing resources comprise:
an output filter adapted to detect differences in the pattern frequency signal according to the pattern which indicate motion in the sensor field.

40. The sensor of claim 39, wherein the output filter blocks frequencies below about 0.5 Hertz.

41. The sensor of claim 35, wherein the signal processing resources comprise:
an output filter adapted to detect differences in the pattern frequency signal according to the pattern which indicate vibration in the sensor field.

42. The sensor of claim 41, wherein the output filter blocks frequencies below about 20 Hertz.

43. The sensor of claim 35, wherein the receiver includes an in-phase channel and a quadrature phase channel.

44. The sensor of claim 43, including a transmit antenna, an in-phase receive antenna and a quadrature phase receive antenna.

45. The sensor of claim 44, wherein the transmitted bursts have a transmit frequency above about 1 gigaHertz, and including an antenna horn having a focal point, and wherein the in-phase receive antenna and the quadrature phase receive antenna comprise antenna elements mounted at respective locations inside the horn, within about $\lambda/8$ at the transmit frequency of the focal point of the horn.

46. The sensor of claim 35, wherein the pattern establishes a plurality of range cells, and the signal processing resources demultiplex the combined output to provide sensor output signals for the plurality of range cells.

47. The sensor of claim 35, wherein the radio frequency oscillator includes a transistor having a source, a gate and a drain, and
a burst width control circuit coupled to the source and drain, which starts a burst by lowering a voltage on the source of the transistor, and a ends a burst by decreasing voltage on the drain of the transistor.

48. The sensor of claim 47, including a damping resistor coupled to the drain of the transistor, and a damping resistor coupled to the source of the transistor.

49. The sensor of claim 35, wherein the radio frequency oscillator includes a transistor having an emitter, a base and a collector, and
a burst width control circuit coupled to the source and drain, which starts a burst by lowering a voltage on the emitter of the transistor, and ends a burst by decreasing voltage on the collector of the transistor.

50. The sensor of claim 49, including a damping resistor coupled to the collector of the transistor, and a damping resistor coupled to the emitter of the transistor.

51. The sensor of claim 35, wherein the receiver includes an in-phase channel and a quadrature phase channel.

52. The sensor of claim 51, including a transmit antenna, an in-phase receive antenna and a quadrature phase receive antenna.

53. The sensor of claim 52, including an antenna horn having a focal point, and wherein the in-phase receive antenna and the quadrature phase receive antenna comprise antenna elements mounted at respective locations inside the horn, within about $\lambda/8$ at the transmitter frequency of the focal point of the horn.

54. The sensor of claim 35, wherein the pattern establishes a plurality of range cells, and the signal processing resources demultiplex the combined output to provide sensor output signals for the plurality of range cells.

55. A method for detecting disturbance in a sensor field, comprising:
transmitting a sequence of transmitted bursts of electromagnetic energy to produce a sensor field, the transmitted bursts having burst widths which vary according to a pattern;
receiving a combination of the transmitted bursts and reflections of the transmitted bursts and producing a combined output; and processing the combined output to generate a sensor output signal indicating variations in differences in the combined output due to the pattern of varying burst widths.

56. The method of claim 55, wherein the transmitted bursts have a frequency between about 900 megaHertz and 24 gigaHertz, and including:

varying the burst widths of the transmitted bursts in the sequence of transmitted bursts so that the transmitted bursts have burst widths in a range of about 2 to 100 nanoseconds which between about 1 and 10 nanoseconds of a maximum burst width for the sequence of transmitted bursts according to the pattern.

\* \* \* \* \*